United States Patent [19]
Toppo

[11] Patent Number: 6,048,903
[45] Date of Patent: Apr. 11, 2000

[54] TREATMENT FOR BLOOD CHOLESTEROL WITH TRANS-RESVERATROL

[75] Inventor: Frank Toppo, Las Vegas, Nev.

[73] Assignees: Robert Toppo, Lake Forest, Calif.; Shaina Toppo, Las Vegas, Nev.

[21] Appl. No.: 08/238,214

[22] Filed: May 3, 1994

[51] Int. Cl.[7] .................................................. A61K 31/05
[52] U.S. Cl. ........................................... 514/733; 514/824
[58] Field of Search ..................................... 514/733, 824

[56] References Cited

PUBLICATIONS

"Ethanol Stimulates Apolpoprotein A–I Secretion by Human Hepatocytes: Implications for a mechanism for Atheroscle-roisis Protection", Metabolism vol. 41,#8, Aug. 1992, pp. 827–832.

Chemical Abstracts 116: 254401 (1992), Siemann et al.
Chemical Abstracts 103: 70127 (1985), JP 60009455.
Chemical Abstracts 97: 85090 (1982), Arichi et al.

*Primary Examiner*—Minna Moezie
*Attorney, Agent, or Firm*—Charles H. Thomas

[57] ABSTRACT

The level of heavy density lipoproteins (HDL) in the blood of a human subject can be in eased by administering dosages of between 50 and 1,000 milligrams of trans-resveratrol to the subject daily. This same dosage reduces the level of light density lipoproteins (LDL) in the blood of the subject. By increasing the blood level of HDL and decreasing the blood level of LDL in the subject, the risk of hypercholesterolemia in the subject is reduced.

4 Claims, 5 Drawing Sheets apo AI (ELISA)

| Concentration (uM) | apo AI (ug/mg protein) | %Baseline |
|---|---|---|
| 0.0 (DMSO) | 7.8 | 100 |
| 0.68 | 7.7 | 99 |
| 4.4 | 8.0 | 103 |
| 44.0 | 10.2 | 131 |
| 88.0 | 12.3 | 157 |
| 220.0 | 3.1 | 40 |

FIG. 1 apo AI mRNA

| Concentration (uM) | mRNA Scanning (apoAI/GAPDH) (AU/mm) | % Control |
|---|---|---|
| 0.0 (DMSO) | 4.196 | 100 |
| 0.68 | 4.965 | 118 |
| 4.4 | 5.822 | 138.8 |
| 44.0 | 8.215 | 195.8 |
| 88.0 | 8.146 | 194.1 |
| 220.0 | 7.361 | 175.4 |

FIG. 2

RESULTS

| Concentration (uM) (mg/L) | Cell Protein (mg) | apo AI (CPM/mg prot.) | % Control | TCA Precipitated Total Protein Secreted (CPM/mg protein) | % Control | apo AI as percent of total protein |
|---|---|---|---|---|---|---|
| 0.0 (DMSO Control) | 1.909 | 1048 | 100 | 33,751 | 100 | 3.1 |
| 0.68* (0.168) | 1.978 | 1039 | 99 | 34,336 | 102 | 3.0 |
| 4.4* (1.0) | 1.993 | 1076 | 103 | 35,785 | 106 | 3.0 |
| 44* (10.0) | 2.010 | 1292 | 123 | 32,690 | 97 | 4.0 |
| 88* (20.0) | 1.957 | 1524 | 145 | 34,302 | 102 | 4.4 |
| 220* (50.0) | 1.135 | 193 | 18 | 6,459 | 19 | 3.0 |

*: All test samples were dissolved in 0.1% dimethylsulfoxide (DMSO).
Data represent mean of triplicate samples.

FIG. 3

RESULTS

| Concentration (uM) | Cell Protein (mg) | apo AII (CPM/mg prot.) | % Control | TCA Precipitated Total Protein Secreted (CPM/mg protein) | % Control | apo AII as percent of total protein |
|---|---|---|---|---|---|---|
| 0.0 (DMSO Control) | 1.909 | 329 | 100 | 33,751 | 100 | 0.97 |
| 0.68* | 1.978 | 381 | 116 | 34,336 | 102 | 1.11 |
| 4.4* | 1.993 | 408 | 124 | 35,785 | 106 | 1.14 |
| 44* | 2.010 | 385 | 117 | 32,690 | 97 | 1.18 |
| 88* | 1.957 | 437 | 133 | 34,302 | 102 | 1.27 |
| 220* | 1.135 | 107 | 32.5 | 6,459 | 19 | 1.66 |

*: All test samples were dissolved in 0.1% dimethylsulfoxide (DMSO).
Data represent mean of triplicate samples.

FIG. 4

RESULTS

| Concentration (uM) | Cell Protein (mg) | apo B (CPM/mg prot.) | % Control | TCA Precipitated Total Protein Secreted (CPM/mg protein) | % Control | apo B as percent of total protein |
|---|---|---|---|---|---|---|
| 0.0 (DMSO Control) | 1.909 | 2867 | 100 | 33,751 | 100 | 8.5 |
| 0.68* | 1.978 | 2996 | 104 | 34,336 | 102 | 8.7 |
| 4.4* | 1.993 | 2819 | 98 | 35,785 | 106 | 7.9 |
| 44* | 2.010 | 1829 | 64 | 32,690 | 97 | 5.6 |
| 88* | 1.957 | 843 | 69 | 34,302 | 102 | 2.5 |
| 220* | 1.135 | 134 | 4.7 | 6,459 | 19 | 2.1 |

All test samples were dissolved in 0.1% dimethylsulfoxide (DMSO).
Data represent mean of triplicate samples.

FIG. 5

TREATMENT FOR BLOOD CHOLESTEROL WITH TRANS-RESVERATROL

BACKGROUND OF THE INVENTION

1. Field of the Invention

The present invention relates to a method of raising the level of heavy density lipoproteins (HDL) and reducing the level of light density lipoproteins (LDL) in the blood of human subjects.

2. Description of the Prior Art

It has been well established that the levels of heavy density lipoproteins (HDL) and light density lipoproteins (LDL) in the blood levels of human beings affect the risk of clogging of the arteries, which in turn can lead to myocardial infarctions, that is, heart attacks. HDLs are the "good" cholesterol which help clear artery clogging. Human subjects whose blood levels contain higher levels of HDL are less likely to experience clogging of the arteries than are human subjects who have lower levels of HDL. Conversely, human subjects whose levels of LDL are elevated are more likely to experience clogging of the arteries, and resultant heart disease, as contrasted with patients whose blood levels of LDL are lower.

Each year millions of human beings suffer from the sequelae of hypercholesterolemia. Examples of the afflictions include hypertension, coronary artery disease, congestive heart failure, peripheral vascular disease, aneurysms, and death due at least in part to these conditions. The risk of such diseases can be reduced by increasing the level of HDL in the blood and/or decreasing the level of LDL in the blood.

Epidemeologists have observed that individuals who drank a half liter of red wine per day significantly increased their blood levels of HDL. White wine has no such effects. The main difference between red and white wines is that red wine is fermented along with the grape skins, while white wine is not.

According to the invention, red and white wine were analyzed. The results of this analysis revealed that there are four ingredients with biological activity which are found only in red wine, and not in white wine. These are: caffeic acid, catechin, quercetin, and trans-resveratrol. According to the present invention, it has been determined that trans-resveratrol does indeed increase the level of HDL and reduce the level of LDL in human blood.

SUMMARY OF THE INVENTION

According to the invention the level of high density cholesterol in a human subject is raised by administering to the subject a quantity of trans-resveratrol ($C_{14}H_{12}O_3$) in dosages of between about fifty and one thousand milligrams on a daily basis. The preferred dossage is about five hundred milligrams. The trans-resveratrol may be administered either orally in the form of a pill or encased in a gel capsule, or transdermally utilizing a patch applied to the skin.

In order to experience the positive effect of trans-resveratrol on HDL level by administering the trans-resveratrol in its natural state in red wine, a person would have to consume at least one half liter of red wine per day. While subjects might well be disposed to cooperate in such administration, such a treatment would likely be more hazardous than the disease (dyslipoproteinemia).

Caffeic acid, catechin, and quercetin are commercially available. However, these substances do not appear to significantly affect the level of either HDL or LDL in human blood. Trans-resveratrol is not commercially available. Therefore, it is necessary to synthetically prepare trans-resveratrol for use in administration to human subjects.

DETAILED DESCRIPTION OF THE INVENTION

To synthesize trans-resveratrol, it was necessary to first prepare a quantity triphenylphosphine salt, also known as Wittig salt. To this end ten grams of 63.86 mmol. concentration, density equal to 1.155, 8.66mL, molecular weight 156.60 methoxy benzyl chloride, and 18.43 grams triphynyphosphine, φ3P, $C_{18}H_{15}P$, molecular weight equal to 262.32 (110 mol %, 70.25 mmol concentration) were both added to benzene (150 mL). Twenty milligrams of potassium iodide were then added. The solution was stirred at reflux for one week. The solution was filtered. The precipitate was then collected and dried under vacuum. The molecular diagram for the reaction is indicated below.

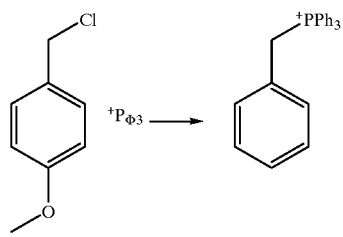

The net weight of the salt collected was 22.38 grams, 53.4 mmol 83% yield.

7.33 grams, 17.4 mmol of the Wittig salt produced as aforesaid was suspended in approximately 150 mL diethyl ether. About 5 mL normal-butyl-lithium (nBuLi) approximately 1M was added at room temperature. This started the persistence of an orange color. 15 mL more of the nBuLi was added. Since there was still some undissolved white solid, another 2 mL nBuLi was added, but the undissolved solid remained. Then, 2.9 gm, 17.7 mmol, of aldehyde was added. This caused the orange color to disappear. The solution was then stirred under nitrogen gas. The molecular diagram of the reaction that occurred is indicated below.

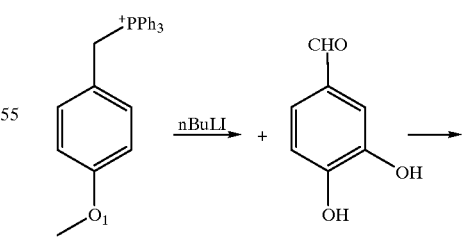

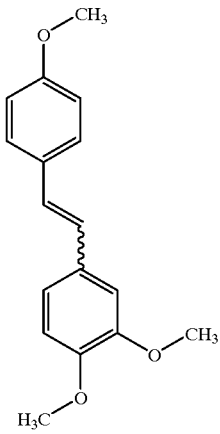
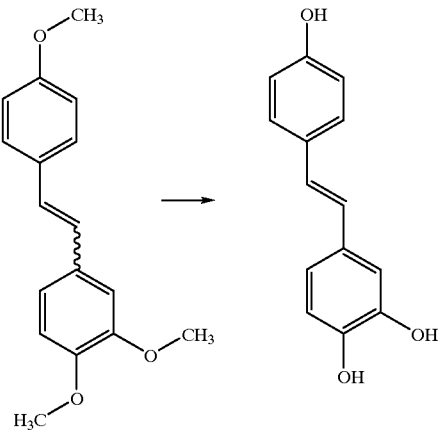

Afterward, the solution exhibited a yellow-orange color. Water was added and the solvent was evaporated. The residue was dissolved into $CH_2Cl_2$ and partitioned or stratified with about 100 mL water. Fifteen milligrams of sodium dihydrogen phosphate was added and the organic layers were separated. The aqueous layer was extracted one more time and then the organic solution was dried over sodium sulfate. The solution was diluted with an equal volume of petroleum ether to make 100 mL total. One hundred fifty mL of silica gel was dissolved in 1:1 dichloromethane and petroleum ether and the product solution filtered through the silica gel. The first two fractions contained the product. Upon evaporation they yielded 3.83 gm, 14.2 mmol, 82% trimethylresveratrol.

3.3 gm (13.6 mmol) trimethylresveratrol was dissolved into 150 mL $CH_2Cl_2$ chilled on dry ice under nitrogen gas. Then, boron tribromide ($BBr_3$) (41 mmol, 10.2 gm 3.9 mL) was added. The color changed to a dark orange and did not change overnight. The orange solution was poured onto approximately 500 mL ice.

When the ice had melted, stirring yielded a three phase system. The unfiltered solution was extracted with ethyl acetate in two batches. The organic layer was denser than the water. The combined aqueous layer was then extracted with $CHCl_3$ with about 20 mL ethyl acetate, and the combined organics dried with $Na_2SO_4$. This solution was then evaporated in vacuo.

Thin layer chromatography of this solution showed one major spot at Rf 0.4 on silica in 9:1 $CHCl_3$:MeOH. Two grams of off white solid appeared on evaporation. After flushing the flask with nitrogen, about 30 mL chloroform was added and the flask heated to attempt triturating out the impurities. However, on heating the solid discolored to orange, and the chloroform did not appear to be dissolving any of the color. Therefore, the chloroform was evaporated in vacuo.

The solid was dissolved in minimal boiling ethanol, but on chilling, even on ice, nothing precipitated. When chloroform was added, a precipitate formed. This was filtered to yield 1.2 gram white solid (5.26 mmol., 38%). An NMR (nuclear magnetic resonance) spectrum confirmed the structure of trans-resveratrol. The reaction is indicated in the molecular diagram below.

Hep-G2 Culture

The human hepatoma line, Hep-G2, has been well characterized as an accurate model in which to study human lipoprotein metabolism. Hep-G2 cells were cultured in 50-mL flasks (Nunc, Thomas Scientific, Swedesboro, N.J.) in 5 mL Dulbecco's modified Eagle's medium (DMEM)/high glucose containing 20% fetal bovine serum ([FBS], heat-inactivated), 1% glutamine/penicillin-streptomycin, and 1% fungizone. All cell culture biologicals were from Irvine Scientific, Irvine, Calif. Cells were maintained in a humidified, 5% $CO_2$ atmosphere at 37 degrees Centigrade. Cells were cultured preconfluent and grew to confluency during the experiment.

Hep-G2 Incubation with Trans-resveratrol

Hep-G2 cells were cultured in separate flasks and incubated for 96 hours in the presence of various concentrations of trans-resveratrol, respectively. The culture medium in each flask was changed every 24 hours. For the experiment wherein the incorporation of $^3H$-leucine into apo A-1 and albumin was measured, Hep-G2 cells were incubated for 72 hours in the presence of trans-resveratrol. The media were changed every 24 hours and an additional trans-resveratrol concentration of 500 mmol/L was used.

Apolipoprotein (apo) A-I is the major protein of high density lipoproteins. Apo A-I effluxes cholestrol from cells and is an important component of the reverse cholesterol transport pathway, a process by which excess body tissue cholesterol is eliminated from the body. Thus, low levels of HDL and apo A-I are associated with increased risk for coronary disease and high levels are cardioprotective. Pharmacologic agents that raise HDL and, especially its physiologically important protein (apo A1), would be expected to be potent antiatherosclerotic agents. This has been documented by M. L. Kashypap in the American Journal of Cardiology, volume 83:56H, 1989.

Apo-B is the major protein of the atherogentic lipoproteins (e.g., LDL). High levels of apo-B are associated with increased risk for coronary disease. Decreasing LDL cholesterol and also apo-B is associated with a reduction in coronary risk and regression of coronary atherosclerosis.

The effect of trans-resveratrol on human hepatic production of apo A-I was studied using the following methods: human repatocytes (Hep-G2 cell line) were cultured by the method described fully in the publication, *Metabolism* 41 (8): pages 827–832, 1992.

After the preincubation step previously described the Hep-G2 cultures were incubated with increasing concentrations of trans-resveratrol after a preincubation period of 48 hours.

Apo A-I Measurement

The mass of apo A-I in the medium was measured by enzyme-linked immunoassay (ELISA) using monospecific monoclonal antibody against apo A-I. Specifically, at the end of 96 hours, with the media being changed every 24 hours, the culture medium from each flask previously described was assayed for apo A-I. A 50 microliter sample of culture medium from each flask was assayed for apo A-I by enzyme-linked immunoassay using the apo A-I monospecific monoclonal antibody, HB-22, developed in the lab, and measured in terms of total cellular genomic DNA. DNA was isolated and absorbance was measured at 260 nanometers. In a repeat experiment, a 1.5-mL sample of culture medium for each flask was lyophilized, reconstituted with 75 microliters of electrophoresis buffer, and then assayed for apo A-I by a modification of Laurell's electroimmunoassay method using an apo A-I polyclonal antibody that was confirmed for monospecificity. Apo A-I was measured in terms of total cellular protein as determined by the method of Lowry et al after cell lysis with 0.5 mL 0.1N NaOH.

Incorporation of $^3$H-Leucine into APO A-I and Albumin

The synthesis of apo A-I, A-II and B was assessed by rate of incorporation of $^3$H-leucine over 24 hour periods into each apo protein secreted into the medium by immunoprecipitation using the specific antibodies indicated. Specifically, after 72 hours incubation with trans-resveratrol as previously described, the media being changed every 24 hours, liver cells were cultured for 2 hours in a medium containing 5 microcentiliters/mL $^3$H -leucine and a 100 microliter sample of the medium was taken. Two hundred microliters phosphate-buffered saline ([PBS], pH 6.8) and 100 microliters sheep anti-human apo A-I polyclonal antiserum were added to the sample. The sample was then incubated for 48 hours at 4 degrees Centigrade.

One hundred microliters rabbit anti-sheep gamma globulin polyclonal antiserum obtained from Sigma in St. Louis, Mo. was added to the sample, which was further incubated for 24 hours at 4 degrees Centigrade. The sample was then centrifuged at 2,000×g for 15 minutes. The immune complex pellet was washed five times with PBS (containing 0.1% sodium dodecylsulfate) and dissolved in 1N NaOH.

The sample was added to 5 mL scintillation fluid manufactured by Scintiverse, Fisher, Pittsburgh, Pa., and radioactivity was counted using a liquid scintillation counter Model LS 5801 manufactured by Beckman Instruments of Fullerton, Calif. The same procedure was used to measure the incorporation of $^3$H-leucine into albumin, using goat anti-human albumin polyclonal antiserum and rabbit anti-goat gamma globulin polyclonal antiserum.

Cholesterol Efflux Measurement

To determine the effects of trans-resveratrol on human cholesterol, data was standardized using cell protein mass. The effects on messenger RNA for apo A-I were studied by the standard technique of Northern Hybridization using specific cDNA probe for apo A-I. A 5-mL sample of culture medium from each of four flasks in which the Hep-G2 culture was prepared was lyophilized and reconstituted to 1.0 mL. This step ensured the evaporation of all trans-resveratrol present in the culture media.

Samples were then assayed in triplicate for their ability to efflux free cholesterol by modifications of both the method of Fielding and Fielding and the method of Rothblatt et al. Cultured human fibroblasts (Coriell Institute, Camden, N.J., Rep. GM00408C) were labelled with $^3$H-free cholesterol for 72 hours. The medium was then removed and cells were washed with fresh medium. Fibroblasts were then transferred to well cultured plates and incubated for an additional 24 hours. This was to ensure that the radiolabelled cholesterol was homogeneously incorporated throughout the cytoplasmic matrix. Previous experiments had been conducted to ensure that the specific activity of the free cholesterol remained constant during the efflux experiment, indicating that the effluxed cholesterol was not derived from specific pools, e.g., from the membrane only.

Non-specific radiolabelled free cholesterol was removed by a preincubation step with 3% bovine serum albumin, obtained from Sigma of St. Louis, Mo., in minimal essential medium. After incubation with the control and experimental efflux medium (containing the incubation medium from the Hep-G2 culture) for one hour, the appearance of radiolabelled free cholesterol into the culture medium was measured. The amount of radioactivity remaining in the fibroblasts was determined after cell lysis. Cholesterol efflux was expressed as a percent of labelled tissue cholesterol that appeared in the medium per milliliter incubation medium per hour.

After testing all four of the biologically active components in red wine, namely caffeic acid, catechin, quercetin, and trans-resveratrol, the results showed that trans-resveratrol alone positively affected all of the measured parameters.

The results of the foregoing are set forth in FIGS. 1, 2, 3, and 4.

BRIEF DESCRIPTION OF THE DRAWINGS

FIG. 1 is a chart showing the progressive increase in apo A-I in the medium containing trans-resveratrol in different concentrations relative to a control.

FIG. 2 is a chart showing the increase in messages RNA for apo A-I in the medium containing trans-resveratrol in different concentrations relative to a control.

FIG. 3 is a chart showing the $^3$H-leucine incorporation into apo A-I in the same concentrations as in FIG. 1.

FIG. 4 is a chart showing apo A-II encorporation in the medium containing trans-resveratrol in different concentrations relative to a control.

FIG. 5 is a chart showing the progressive decline of apo-B in the medium containing trans-resveratrol in different concentrations relative to a control.

Trans-resveratrol in concentrations of 0, 0.17, 1.0, 10.0, 20.0, and 50.0 mg/L was associated with progressive increase in apo A-I in the medium. As indicated is FIG. 1, this increase as a percentage of the control, (that is, the zero concentration value), was 100, 99, 103, 131, 157, and 40 percent. Using the same concentrations $^3$H-leucine incorporation into apo A-I was 100 (control), 99, 103, 145, and 18 percent, respectively, as shown in FIG. 3. Incorporation of apo A-II as shown in FIG. 4 was 100, 116, 124, 117, 133, and 32 percent, respectively. As shown in FIG. 5, apo-B incorporation showed a progressive decline and was 100, 104, 98, 64, 69, and 5 percent, respectively. No appreciable change was observed in $^3$H-leucine incorporation into total proteins secreted into the medium, as assessed by trichloracetic acid precipitation. The messenger RNA for apo A-I increased from 100, which was the baseline control, to 118, 139, 196, 194, and 175 percent, respectively, as set forth in FIG. 2.

The foregoing data confirms that the synthesized trans-resveratrol in doses of 50 to 1,000 mg stimulates hepatic production of apo A-I and A-II, major proteins of anti-atherogenic high density lipoproteins. The data also confirmed that the synthesized trans-resveratrol also decreases apo-B, a major protein of atherogenic low density and very low density (LDL and VLDL, respectively) lipoproteins.

Undoubtedly, numerous variations and modifications of the invention will become readily apparent to those familiar with blood cholesterol control in human subjects. Accordingly, the scope of the invention should not be construed as limited to the specific implementation of the method described.

I claim:

1. A method of raising the level of high density cholesterol and reducing the level of low density cholesterol in a human subject comprising administering to said subject between about 50 milligrams and about 1000 milligrams of trans-resveratrol daily.

2. A method according to claim 1 wherein said trans-resveratrol is administered orally.

3. A method according to claim 1 wherein said trans-resveratrol is administered transdermally.

4. A method according to claim 1 comprising administering at least about 500 milligrams of trans-resveratrol daily.

* * * * *